United States Patent
Matsuda et al.

(10) Patent No.: US 10,849,902 B2
(45) Date of Patent: Dec. 1, 2020

(54) MEDICAMENT FOR TREATING HEART FAILURE

(71) Applicant: TAKEDA PHARMACEUTICAL COMPANY LIMITED, Osaka (JP)

(72) Inventors: Takahisa Matsuda, Kanagawa (JP); Takashi Motoyaji, Kanagawa (JP); Shuji Kitamura, Kanagawa (JP); Masato Yoshida, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 142 days.

(21) Appl. No.: 16/065,362

(22) PCT Filed: Dec. 21, 2016

(86) PCT No.: PCT/JP2016/088121
§ 371 (c)(1),
(2) Date: Jun. 22, 2018

(87) PCT Pub. No.: WO2017/110881
PCT Pub. Date: Jun. 29, 2017

(65) Prior Publication Data
US 2020/0054637 A1 Feb. 20, 2020

(30) Foreign Application Priority Data
Dec. 25, 2015 (JP) .................... 2015-253809

(51) Int. Cl.
*A61K 31/517* (2006.01)
*A61K 31/519* (2006.01)
*A61P 9/04* (2006.01)

(52) U.S. Cl.
CPC ............ *A61K 31/519* (2013.01); *A61P 9/04* (2018.01)

(58) Field of Classification Search
CPC .................................................. A61K 31/517
USPC ..................................................... 514/259.3
See application file for complete search history.

(56) References Cited

U.S. PATENT DOCUMENTS

| | | |
|---|---|---|
| 7,514,441 B2 | 4/2009 | Yasuma et al. |
| 9,447,100 B2 | 9/2016 | Yasuma et al. |
| 2004/0242602 A1 | 12/2004 | Gungor et al. |
| 2006/0079536 A1 | 4/2006 | Yasuma et al. |
| 2009/0304821 A1 | 12/2009 | Notoya et al. |
| 2015/0266872 A1 | 9/2015 | Koike et al. |

FOREIGN PATENT DOCUMENTS

| | | |
|---|---|---|
| CN | 1771231 A | 5/2006 |
| CN | 104910118 A | 9/2016 |
| EP | 3437644 A1 | 2/2019 |
| JP | 2005-239611 A | 9/2005 |
| JP | 2005239611 A | 9/2005 |
| JP | 2006-510582 A | 3/2006 |
| WO | 2004/017908 A2 | 3/2004 |
| WO | 2013/113860 A1 | 8/2013 |
| WO | 2014/061676 A1 | 4/2014 |
| WO | 2017/170354 A1 | 10/2017 |

OTHER PUBLICATIONS

International Search Report for Application No. PCT/JP2016/088121 dated Mar. 14, 2017 (5 pages).
Yamamura, "Pathological function of Ca2+-sensing receptor in pulmonary arterial hypertension," J. Smooth Muscle Res., 2014, 50:8-17.
Lu et al., "Role of the Calcium-Sensing Receptor in Cardiomyocyte Apoptosis via the Sarcoplasmic Reticulum and Mitochondrial Death Pathway in Cardiac Hypertrophy and Heart Failure," Cell Physiol Biochem, 2013, 31:728-743.
Yoshida et al., "Novel and potent calcium-sensing receptor antagonists: discovery of (5R)-N-[1-ethyl-1-(4-ethylphenyl) propyl]-2,7,7-trimethyl-5-phenyl-4,5,6,7-tetrahydropyrazolo[1,5-a]pyrimidine-3-carboxamide monotosylate (TAK-075) as an orally active bone anabolic agent," Bioorganic & Medical Chemistry, 2011, 19:1881-1894.
Sun et al., "Calcium-sensing receptor: a sensor and mediator of ischemic preconditioning in the heart," Am J Physiol Heart Cir Physiol, 2010, 299:H1309-H1317.
Tfelt-Hansen et al., "Calcium receptor is functionally expressed in rat neonatal ventricular cardiomyocytes," Am J Physiol Heart Circ Physiol, 2006, 290:H1165-H1171.
Liu et al., "Rat Parathyroid Hormone 1-34 Signals through the MEK/ERK Pathway to Induce Cardiac Hyperthrophy," The Journal of International Medical Research, 2008, 36:942-950.
Zhang et al., "Calcium Sensing Receptor Promotes Cardiac Fibroblast Proliferation and Extracellular Matrix Secretion," Cell Physiol Biochem, 2014, 33:557-568.
Liu et al., "Calhex231 Ameliorates Cardiac Hypertrophy by Inhibiting Cellular Autophagy in Vivo and in Vitro," Cell Physiol Biochem, 2015, 36:1597-1612.
Zaruba et al., Parathyroid hormone treatment after myocardial infarction promotes cardiac repair by enhanced neovascularization and cell survival, Cardiovascular Research, 2008, 77:722-731.
Brunner et al., "The cardioprotective effects of parathyroid hormone are independent of endogenous granulocyte-colony stimulating factor release," Cardiovascular Research, 2012, 93:330-339.
Tastan et al., "Parathyroid hormone improves contractile performance of adult rat ventricular cardiomyocytes at low concentrations in a non-acute way," Cardiovascular Research, 2009, 82:77-83.

(Continued)

*Primary Examiner* — Raymond J Henley, III
(74) *Attorney, Agent, or Firm* — Michael Best & Friedrich LLP

(57) ABSTRACT

The present invention provides a medicament for preventing or treating heart failure. More specifically, the present invention provides a medicament for preventing or treating heart failure, comprising a compound selected from the group consisting of (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide and salts thereof.

6 Claims, 1 Drawing Sheet

(56) References Cited

OTHER PUBLICATIONS

Cha et al., "Parathyroid hormone accelerates decompensation following left ventricular hypertrophy," Experimental and Molecular Medicine, 2010, 42(1):61-68.
Smogorzewski et al., "Parathyroid hormone increases cytosolic calcium concentration in adult rat cardiac myocytes," Am J Physiol Heart Circ Physiol, 1993, 264:H1998-H2006.
Li et al., "Role of Calcium-Sensing Receptor in Cardiac Injury of Hereditary Epileptic Rats," Pharmacology, 2015, 95:10-21.
Guo et al., "Inhibition of the Ca2+-sensing receptor rescues pulmonary hypertension in rats and mice," Hypertens Res, 2014, 37(2):116-124.
Schepelmann et al., "The vascular Ca2+-sensing receptor regulates blood vessel tone and blood pressure," Am J Physiol Cell Physiol, 2016, 310:C193-C204.
Tang et al., "Pathogenic role of calcium-sensing receptors in the development and progression of pulmonary hypertension," Am J Physiol Lung Cell Mol Physiol, 2016, 310(5):L846-L859.
Yamamura et al., "Calcilytics enhance sildenafilinduced antiproliferation in idiopathic pulmonary arterial hypertension," Eur J Pharmacol, 2016, 784:15-21.
Yamamura et al., "Dihydropyridine Ca2+ Channel Blockers Increase Cytosolic [Ca2+] by Activating Ca2+-sensing Receptors in Pulmonary Arterial Smooth Muscle Cells," Circ Res, 2013, 112(4):640-650.
Yamamura et al., "Enhanced Ca2+-Sensing Receptor Function in Idiopathic Pulmonary Arterial Hypertension," Circ Res, 2012, 111(4):469-481.
Yamamura et al., "Enhanced Ca2+-Sensing Receptor Function in Pulmonary Hypertension," J of the Pharmaceutical Society of Japan, 2013, 133(12):1351-1359.
Yoshida et al., "Synthesis and structure-activity relationship of tetrahydropyrazolopyrimidine derivatives—A novel structural class of potent calcium-sensing receptor antagonists," Bioorg Med Chem, 2010, 18(24):8501-8511.
Yoshida et al., "Discovery of Novel and Potent Orally Active Calcium-Sensing Receptor Antagonists that Stimulate Pulselike Parathyroid Horone Secretion: Synthesis and Structure-Activity Relationships of Tetrahydropyrazolopyrimidine Denvates," J Med Chem, 2011, 54(5):1430-1440.
Written Opinion for Application No. PCT/JP2017/012305 dated May 16, 2017 (8 pages, English translation).
International Search Report for Application No. PCT/JP2018/016995 dated Jun. 12, 2018 (4 pages).
International Search Report for Application No. PCT/JP2017/012305 dated May 16, 2017 (5 pages).
International Search Report for Application No. PCT/JP2018/016996 dated Jun. 19, 2018 (4 pages).
European Patent Office Extended Search Report for Application No. 16878768.7 dated Aug. 5, 2019 (8 pages).
European Patent Office Extended Search Report for Application No. 17774891.0 dated Oct. 29, 2019 (7 pages).
Yamamura et al., "Inhibition of Excessive Cell Proliferation by Calcilytics in Idiopathic Pulmonary Arterial Hypertension," PLoS One, 2015, 10(9):e0138384 (16 pages).
Chinese Patent Office Action for Application No. 201680076074.0 dated Apr. 13, 2020 (14 pages, English translation included).
United States Patent Office Notice of Allowance for U.S. Appl. No. 16/608,140 dated Sep. 11, 2020 (13 pages).
Gupta et al., "Animal Models for Heart Failure," Methods in Molecular Medicine, vol. 129: Cardiovascular Disease: Methods and Protocols, vol. 2: Molecular Medicine Edited by: Q. K. Wang, Humana Press Inc., Totowa, NJ, 2007, pp. 97-114.
Schreckenberg et al., "Calcium sensing receptor expression and signalling in cardiovascular physiology and disease," Vascular Pharmacology 107 (2018) 35-42.
Jones et al., "Regulation of Ca2+ signaling in transgenic mouse cardiac myocytes overexpressing calsequestrin," J Clin Invest. 1998, 101(7):1385-1393.
Wang et al., "Murine models for the study of congestive heart failure: Implications for understanding molecular mechanisms and for drug discovery," Journal of Pharmacological and Toxicological Methods 50 (2004) 163-174.

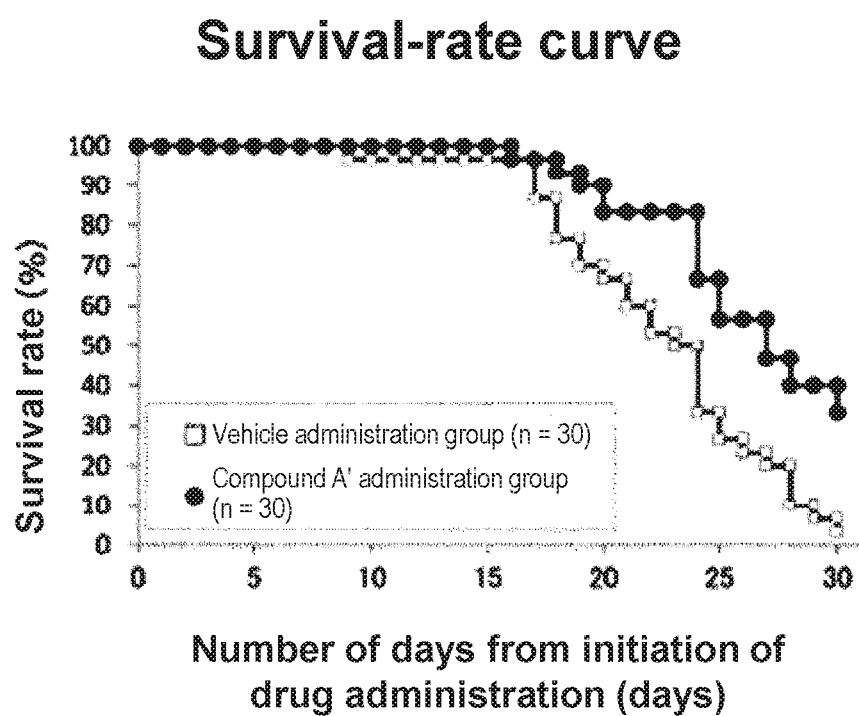

MEDICAMENT FOR TREATING HEART FAILURE

CROSS-REFERENCE TO RELATED APPLICATIONS

This is a U.S. national stage entry of International Patent Application No. PCT/JP2016/088121, filed on Dec. 21, 2016, which claims priority to Japanese Patent Application No. 2015-253809, filed on Dec. 25, 2015, the entire contents of all of which are fully incorporated herein by reference.

TECHNICAL FIELD

The present invention relates to a medicament for preventing or treating heart failure.

BACKGROUND OF THE INVENTION

Heart failure is a disease characterized by a disease state where cardiac output decreases due to dysfunction of cardiomyocytes and a disease state caused by physical burden brought by a mechanism of maintaining cardiac output. Cardiomyocytes play a role in contraction and relaxation. For the contraction and relaxation, $Ca^{2+}$ ions are required. Contraction of cardiomyocytes proceeds through stages of: an action potential propagating to the transverse tubules to depolarize the transverse tubule membrane; allowing $Ca^{2+}$ ions to flow into cells from a potential-dependent Type L $Ca^{2+}$ channel of the transverse tubules; the inflow $Ca^{2+}$ ions binding to a $Ca^{2+}$ release channel (ryanodine receptor or RYR) of the sarcoplasmic reticulum to release $Ca^{2+}$ ions from the sarcoplasmic reticulum to the cytoplasm; and the released $Ca^{2+}$ ions within the cell binding to troponin C to induce contraction of the cardiomyocytes. Further, relaxation of cardiomyocytes proceeds by taking $Ca^{2+}$ ions into the sarcoplasmic reticulum via a $Ca^{2+}$ release pump (SERCA) to reduce the cytoplasmic level of $Ca^{2+}$ ions and dissociate the $Ca^{2+}$ ions from the troponin C. Accordingly, if something goes wrong in any one of the stages and $Ca^{2+}$ ions are not released into the cytoplasm, cardiomyocytes fail to work, with the result that heart failure occurs.

As a therapeutic drug for heart failure, e.g., a cardiotonic drug such as β blocker, anti-aldosterone drug, a diuretic drug and digitalis, an angiotensin converting enzyme inhibitor and angiotensin II antagonist are used in clinical sites for improvement of short-term symptoms and hemodynamic stabilization. However, these drugs are insufficient to improve the re-hospitalization rate and long-term life prognosis. In recent years, it has been desired to provide a novel heart-failure therapeutic drug for improving re-hospitalization rate and long-term life prognosis.

$Ca^{2+}$ ions (hereinafter also referred to simply as calcium) play an essential role in maintaining/regulating functions of various cells including not only nerve and muscle but also endocrine cells and exocrine cells. Therefore, the blood calcium level is precisely controlled to fall within a narrow range. Parathyroid hormone (PTH) plays a central role in maintaining the blood calcium level. Thus, secretion of PTH from the parathyroid gland must be controlled sensitively in response to a change in blood calcium level. Actually, when blood calcium level changes, blood PTH level rapidly changes in accordance therewith. Brown et al., pointed out the possibility of the existence of the mechanism where the extracellular calcium concentration is sensed by parathyroid cells and the information thereof is transmitted to the cells. In 1993, they successfully cloned a calcium-sensing receptor (CaSR; hereinafter simply referred to as a calcium receptor) from the bovine parathyroid gland and determined the properties thereof (Nature, 366, 575-580 (1993)).

The calcium receptor has the N terminal of 600 amino acids in full length and is constituted of a large-terminal extracellular region having 7 transmembrane regions similarly to other G protein-coupled receptors and an intracellular region having the C terminal consisting of 200 or less amino acids.

If the extracellular calcium concentration increases, phospholipase (PL)-C is activated and then the level of inositol triphosphate ($IP_3$) increases, with the result that the intracellular calcium concentration increases. In this mechanism, PTH secretion is presumably suppressed. If the extracellular calcium concentration is maintained at a high level, the intracellular calcium concentration subsequently and continuously increases. Conceivably, calcium flow-in from outside the cell is also promoted. If the extracellular calcium concentration increases, $PL-A_2$ and D are activated. These are probably activated via, e.g., protein kinase (PK)-C, which is simultaneously activated via a calcium receptor. The calcium receptor suppresses adenylyl cyclase via Gi protein or arachidonic acid production through $PL-A_2$ activation to reduce intracellular cyclic AMP level (Bone, 20, 303-309 (1997)).

It is known that (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide (hereinafter referred to also as "compound A"), (5R)—N-[1-ethyl-1-(4-methoxyphenyl)propyl]-2,7,7-trimethyl-5-phenyl-4,5,6,7-tetrahydropyrazolo[1,5-a]pyrimidine-3-carboxamide (hereinafter referred to also as "compound B") and (5R)—N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide (hereinafter referred to also as "compound C") are involved in regulation of the activity of the calcium-sensing receptor (CaSR) and regulation of parathyroid hormone (PTH) (Patent literature 1 and Patent literature 2). Also, Non patent literature 1 discloses that compound A serves as an antagonist to CaSR (Non patent literature 1).

In Non patent literatures 2 and 3, it is described that cardiac function is improved by treatment with parathyroid hormone; whereas, in Non patent literature 4, it is described that cardiac function is exacerbated by treatment with parathyroid hormone. Thus, the relationship between a parathyroid hormone therapy and improvement of cardiac function has not yet been sufficiently revealed.

In Non patent literature 5, it is described that cardiac hypertrophy is improved by a CaSR inhibitor, i.e., Calhex231, in a transverse aortic constriction (TAC) model; however, it is not elucidated that the drug is effective or not after cardiac function deteriorates. Non patent literature 6 discloses that, if Calhex231 is administered, more specifically, if the drug is administered after the cardiac load is given, cardiac hypofunction is not improved. Further, in Non patent literature 7, it is described that a CaSR antagonist invalidates a cardioprotective effect in an ischemia preconditioning model. Thus, the relationship of CaSR inhibition with improvement of cardiac hypofunction or improvement of survival rate has not yet been sufficiently elucidated.

CITATION LIST

Patent Literature

Patent literature 1: WO2004/017908
Patent literature 2: Japanese Patent Laid-Open No. 2005-239611

Non Patent Literature

Non patent literature 1: Bioorganic & Medicinal Chemistry 19: 1881-1894, 2011

Non patent literature 2: Cardiovascular research, 77: 722-731, 2008

Non patent literature 3: Cardiovascular research, 93: 330-339, 2012

Non patent literature 4: Experimental and molecular medicament 42, 61-68, 2010

Non patent literature 5: Cell Physiol. Biochem., 36: 1597-1612, 2015

Non patent literature 6: Cell Physiol. Biochem., 33: 557-568, 2014

Non patent literature 7: Am. J. Physiol. Heart Circ. Physiol., 299: H1309-H1317, 2010

SUMMARY OF INVENTION

Technical Problem

The present invention provides a medicament for preventing or treating heart failure.

Solution to Problem

The present inventors found that a compound selected from the group consisting of compound A, compound B, compound C and salts thereof is effective in preventing and/or treating heart failure. The present invention was achieved based on the finding.

More specifically, according to the present invention, the following inventions are provided.

[1] A medicament for preventing or treating heart failure, comprising a compound selected from the group consisting of (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide and salts thereof.

[2] The medicament according to the above [1], for treating heart failure.

[3] The medicament according to the above [1], wherein heart failure is acute decompensated heart failure.

[1a] A method for preventing or treating heart failure in a mammal characterized by administering, to a mammal, a compound selected from the group consisting of (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)—N-[1l-ethyl-1-(4-methoxyphenyl)propyl]-2,7,7-trimethyl-5-phenyl-4,5,6,7-tetrahydropyrazolo[1,5-a]pyrimidine-3-carboxamide, (5R)—N-[1l-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide and salts thereof.

[2a] The method according to the above [1a], for treating heart failure.

[3a] The method according to the above [1a], wherein the heart failure is acute decompensated heart failure.

[1b] A compound for preventing or treating heart failure, selected from the group consisting of (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide and salts thereof.

[2b] The compound according to the above [1b], for treating heart failure.

[3b] The compound according to the above [1b], wherein the heart failure is acute decompensated heart failure.

[1c] Use of a compound selected from the group consisting of (5R)—N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)—N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide and salts thereof, for producing a prophylactic or therapeutic agent for heart failure.

[2c] Use according to the above [1c], for treating heart failure.

[3c] Use according to the above [1c], wherein the heart failure is acute decompensated heart failure.

Advantageous Effects of Invention

According to the present invention, it is possible to prevent or treat heart failure.

BRIEF DESCRIPTION OF DRAWINGS

FIG. 1 shows the Kaplan-Meier curve of a heart failure model animal to which compound A' or a vehicle was administered.

DESCRIPTION OF EMBODIMENTS

In the specification, the term "subject" refers to a mammal, for example, a human. In the specification, a "subject with heart failure" refers to a subject suffering from heart failure. If the subject is a human, the subject is referred to as a "patient". If the subject with heart failure is a human, the subject is referred to as "heart failure patient".

In the specification, the term "pharmaceutically acceptable salt" refers to an acid addition salt or base addition salt, which is an acceptable salt if it is administered in a living body.

In the specification, the term "heart failure" refers to a state where output of blood from the heart (hereinafter referred to as "cardiac output") deteriorates and/or a symptom produced by regulatory mechanism of suppressing deterioration in cardiac output and means a physical condition where a sufficient blood circulation volume cannot be ensured. In the specification, the term "treatment of heart failure" refers to improving the state where cardiac output deteriorates and/or the symptom produced by a regulatory mechanism of suppressing deterioration in cardiac output. As a heart failure treatment for improvement of the short-term symptoms and hemodynamics stabilization, e.g., a β blocker and an anti-aldosterone drug are used; however, in the present invention, a decrease of ejection fraction can be suppressed and a survival rate can be improved without using these drugs. Thus, in the present invention, heart failure (more specifically, e.g., deterioration in cardiac output) can be prevented or treated.

In the specification, the term "ejection fraction" (EF), which is a cardiac function evaluation index, is a value obtained by dividing blood volume (ejection volume) fed by the heart per beat by the left ventricular volume at the time of cardiac dilatation. In a subject with heart failure (heart failure patient), a decrease of ejection fraction is observed. Thus, improvement of ejection fraction is one of the goals for heart failure treatment.

The clinical condition of heart failure is classified into four stages depending on the severity thereof by the New York Heart Association (NYHA).

TABLE 1

NYHA Heart Failure Classification

| Class | Patient's symptom |
|---|---|
| Class I | Patients have cardiac disease but without resulting limitation of physical activity. Ordinary physical activity does not cause undue fatigue, palpitations, dyspnea, or anginal pain. |
| Class II | Patients have cardiac disease resulting in slight limitation of physical activity. They are comfortable at rest. Ordinary physical activity results in fatigue, palpitations, dyspnea, or anginal pain. |
| Class III | Patients have cardiac disease resulting in marked limitation of physical activity. They are comfortable at rest. Less than ordinary physical activity results in fatigue, palpitations, dyspnea, or anginal pain. |
| Class IV | Patients have cardiac disease resulting in an inability to carry on any physical activity without discomfort. Symptoms of cardiac insufficiency or of the anginal syndrome may be present even at rest. If any physical activity is undertaken, discomfort is increased. |

* Class IIs: slight limitation of physical activity
Class IIm: Medium limitation of physical activity According to the AHA/ACC stage classification (American Heart Association/American College of Cardiology), the clinical condition of heart failure is classified into four stages depending on the severity thereof.

TABLE 2

AHA/ACC stage classification of heart failure

| Stage | Definition |
|---|---|
| A | Risk factor is present; however, no cardiac dysfunction is observed |
| B | Cardiac contractile dysfunction of left ventricle with no symptom |
| C | Symptomatic heart failure |
| D | Intractable heart failure |

The correspondence relationship between the NYHA classification and the AHA/ACC stage classification is roughly as follows.

TABLE 3

Correspondence relationship between the NYHA classification and the AHA/ACC stage classification

| NYHA class | AHA/ACC stage class |
|---|---|
| — | A |
| Class I | B |
| Class II | C |
| Class III | |
| Class IV | |
| Class IV | D |

In the specification, the term "heart failure" is a disease state different from that of myocardial infarction, and the type of medicament to be used for treatment differs from that of myocardial infarction. More specifically, myocardial infarction refers to ischemic condition (necrosis) of heart muscle, which is caused by a decrease in blood supply to cardiomyocytes due to, e.g., emboli, produced within blood vessel. Because of this, myocardial infarction is treated or prevented by removing emboli or inhibiting embolization; more specifically, by administration of a thrombolytic agent or an antithrombocytic agent, an anti-coagulation method, an anti-ischemic therapy or a hyperlipemia treatment. In contrast, heart failure refers to a state where cardiac output deteriorates and/or the symptom produced by a regulatory mechanism of suppressing deterioration in cardiac output, and treated by e.g., a cardiotonic agent and/or a diuretic agent. Likewise, since the disease states differ, therapies differ. To reiterate, heart failure is a different disease from myocardial infarction. Note that, in the specification, deterioration in cardiac output in a subject with myocardial infarction is included in "heart failure" and can be treated by the present invention. More specifically, some of the subjects with myocardial infarction presumably have heart failure other than myocardial infarction. In the present invention, a disease state caused by heart failure in subjects with myocardial infarction can be prevented or treated.

In the specification, the term "compensated heart failure" generally refers to a state produced in vivo by a regulatory mechanism (compensation mechanism) for maintaining blood circulation in response to deterioration in cardiac output caused by heart failure. Accordingly, compensated heart failure can be prevented or treated by the present invention. Examples of the compensation include compensation according to the Frank-Starling law, compensation by myocardial remodeling and nervous humoral compensation.

(1) Compensation According to the Frank-Starling Law

In the compensation according to the Frank-Starling law, compensation mechanism functions such that deterioration in cardiac output is improved by increasing preload, and increased cardiac output per beat thereby. However, the compensation effect is limited by an increase of arterial pressure. As a result, preload further increases, symptoms such as lung congestion and peripheral edema, are developed.

(2) Compensation by Myocardial Remodeling

When pressure load is applied to cardiomyocytes, the wall thickness of the heart increases and the diameter of the heart ventricle decreases, that is, concentric hypertrophy develops. Concentric hypertrophy herein is a compensation mechanism of maintaining normal contractility against an increase in afterload. However, when the heart muscle of the left ventricle is reduced in retractility due to concentric hypertrophy, even if the circulating blood volume is low, ventricular diastolic pressure increases and congestion occurs.

Due to volume overload on cardiomyocytes, the inner cavity of the heart is enlarged to develop eccentric hypertrophy. In the eccentric hypertrophy, retractility of the ventricle is enhanced and preload decreases and the cardiac output comes to deteriorate.

As described above, if compensation by myocardial remodeling is excessive, heart failure may exacerbate.

(3) Nervous Humoral Compensation

When cardiac output of blood deteriorates due to heart failure, arterial pressure decreases. If so, the sympathetic nerve is activated to release a catecholamine. The catecholamine increases heart rate and cardiac contractility and induces vasoconstriction and renin secretion. When arterial pressure decreases, the pressure of afferent glomerular arteriole of kidney decreases, with the result that secretion of renin from juxtaglomerular cells is accelerated. Renin promotes production of angiotensin II, contracts the artery and increase afterload. Angiotensin II also promotes resorption of sodium ions and water in the kidney, and thus, blood volume increases and preload increases. Angiotensin II further promotes secretion of a catecholamine. This reaction transiently improves blood circulation in a subject with heart failure; however, if sympathetic stimulation lasts for a long term, responsiveness to stimulation becomes poor and the compensation system will not work.

In the present invention, the term "acute heart failure" generally refers to a disease state where an organic and/or functional abnormality occurs in the heart; compensation mechanism by a cardiac pump (function) immediately fails to work; ventricular end-diastolic pressure rises; and perfusion into major organs fails, with the result that symptoms and signs abruptly emerge from these phenomena or are exacerbated. The "acute heart failure" herein includes an acute exacerbation period of chronic heart failure. The acute heart failure is roughly divided into the following six disease states: acute decompensated heart failure, hypertensive acute heart failure, acute cardiogenic pulmonary edema, cardiogenic shock, high-output heart failure and acute right heart failure. In the present invention, acute heart failure can be prevented or treated.

In the present invention, the term "chronic heart failure" generally refers to a state where the cardiac output deteriorates by a chronic myocardial damage and a blood volume satisfying oxygen demand by peripheral organs is neither absolutely nor relatively pumped out, with the result that the lung, systemic venous system or both of them are congested and a problem occurs in daily life. Some of the subjects with chronic heart failure have both heart failure and chronic myocardial damage in combination. Of them, heart failure can be prevented or treated in the present invention.

In the specification, the term "acute decompensated heart failure" generally refers to a new-type acute heart failure, which is associated with mild signs and symptoms of heart failure and fails to satisfy diagnostic criteria such as cardiogenic shock, pulmonary edema and hypertensive acute heart failure, or referred to one with acute exacerbation of chronic heart failure.

In the specification, the term "hypertensive acute heart failure" refers to a disease state caused by hypertension and associated with signs and symptoms of heart failure, acute lung congestion or pulmonary edema.

In the specification, the term "acute cardiogenic pulmonary edema" refers to a disease state where dyspnea and orthotic respiration are observed and rale and pulmonary edema are associated.

In the specification, the term "cardiogenic shock" refers to a serious disease state where microcirculation of the peripheral and systemic major organs is significantly damaged by heart pump failure and sequentially tissue hypoperfusion is developed.

In the specification, the term "high output heart failure" refers to a disease state caused by e.g., thyrotoxicosis, anemia, shunt disease, beriberi heart, Paget's disease and iatrogenic factors and associated with lung congestion although the limbs are warm.

In the specification, the term "acute right heart failure" refers to a disease state of low blood pressure or low cardiac output associated with elevated venous pressure or hepatomegaly.

In the present invention, acute decompensated heart failure can be prevented or treated.

Heart failure includes ischemic heart failure and non-ischemic heart failure.

Ischemic heart failure refers to heart failure caused by losing balance between oxygen demand and supply in the heart muscle. Ischemic heart failure includes those caused by angina pectoris and arteriosclerosis. In the present invention, ischemic heart failure can be prevented or treated.

Non-ischemic heart failure is heart failure except ischemic heart failure. Also in the present invention, non-ischemic heart failure can be treated.

In the specification, "congestive heart failure" generally refers to a disease state where cardiac output deteriorates with swelling in pulmonary and peripheral tissue. Congestive heart failure includes heart failures caused by, for example, arrhythmia, ischemic heart disease, acute myocardial infarction, hypertension, cardiac myopathy, myocarditis, congenital heart disease, and other diseases. Congestive heart failure includes acute heart failure and chronic heart failure. Congestive heart failure can be also prevented or treated by the present invention.

Examples of the symptoms of chronic heart failure include increased fatigue, shortness of breath with motion, anorexia, hypanakinesia, cough, palpitation, lower-leg edema, swelling, body weight gain with swelling, and dyspnea during sleep. The present invention can treat at least one state selected from the above states. Examples of the symptoms of acute heart failure include sudden onset of symptoms of chronic heart failure as mentioned above, dyspnea and muzziness. The present invention can treat at least one state selected from e.g., these states.

In the present invention, a disease state of heart failure in a subject can be prevented or treated by administering a compound selected from the group consisting of compound A, compound B, compound C and salts thereof to the subject.

According to the present invention, there is provided a medicament comprising a compound selected from compound A, B and C and salts thereof, for use in preventing or treating heart failure.

Compound A is represented by the following formula:

[Formula 1]

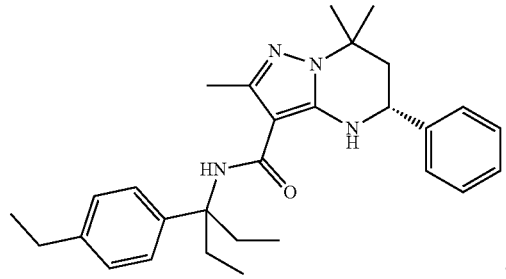

Compound B is represented by the following formula:

[Formula 2]

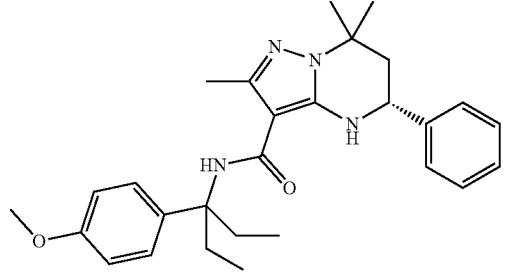

Compound C is represented by the following formula:

[Formula 3]

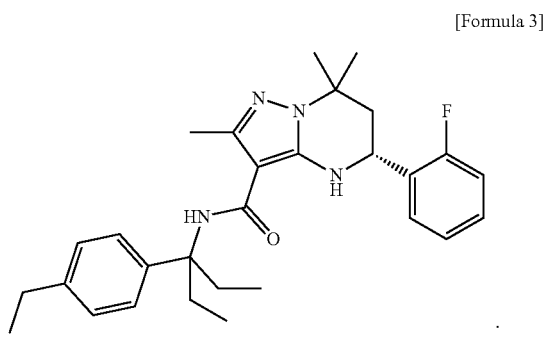 [SMILES: CCc1ccc(C(CC)(CC)NC(=O)c2c(C)nn3c2N[C@@H](c2ccccc2F)CC3(C)C)cc1]

In the present invention, compound A, B and C and salts thereof can be used for preventing or treating heart failure. According to the present invention, there is provided a medicament for use in preventing or treating heart failure and particularly a medicament for use in increasing cardiac output or preventing or treating decrease of cardiac output in a subject with heart failure, comprising a compound selected from the group consisting of compound A, B and C and salts thereof.

In the present invention, compound A, B and C and salts thereof can be used for preventing or treating deterioration in cardiac output in a subject with heart failure. Accordingly, the medicament of the present invention may be a cardio-protective drug comprising a compound selected from compound A, B and C and salts thereof.

In a specific embodiment of the present invention, the medicament of the present invention can be used in preventing or treating ischemic heart failure or non-ischemic heart failure. In a specific embodiment of the present invention, the medicament of the present invention can be used in preventing or treating non-ischemic heart failure. In a further specific embodiment of the present invention, the medicament of the present invention can be used in treating non-ischemic heart failure.

In a specific embodiment of the present invention, the medicament of the present invention can be used in preventing or treating decompensated heart failure. In a specific embodiment of the present invention, the medicament of the present invention can be used in preventing or treating acute heart failure. In a specific embodiment of the present invention, the medicament of the present invention can be used in preventing or treating acute decompensated heart failure. In a further specific embodiment of the present invention, the medicament of the present invention can be used in preventing or treating acute decompensated heart failure.

In the present invention, compound A, B and C and salts thereof improve a decrease of ejection fraction in a subject with heart failure or increases ejection fraction. The medicament of the present invention may be a medicament (improving drug) comprising a compound selected from compound A, B and C and salts thereof, for improving a decrease of ejection fraction and death caused by a decrease of ejection fraction in a subject with heart failure.

In the present invention, compound A, B and C and salts thereof can suppress exacerbation of cardiac function or further exacerbation thereof in a subject with heart failure. The medicament of the present invention may be a medicament comprising a compound selected from compound A, B and C and salts thereof for use in suppressing exacerbation of cardiac function or further exacerbation thereof in a subject with heart failure. The medicament of the present invention may be a medicament comprising a compound selected from compound A, B and C and salts thereof for protecting the heart in a subject with heart failure. In the present invention, compound A, B and C and salts thereof can reduce cardiac load and suppress cardiac hypertrophy, interstitial fibrosis and an increase of apoptosis in a subject with heart failure. The medicament of the present invention may be a medicament comprising a compound selected from compound A, B and C and salts thereof, for use in treating at least one (disease) state selected from an increase of cardiac load, cardiac hypertrophy, interstitial fibrosis and/or an increase of cardiomyocyte apoptosis, in a subject with heart failure.

In a specific embodiment of the present invention, the medicament of the present invention can be used in preventing or treating Class I, II, III or IV-stage heart failure according to the NYHA classification. In a specific embodiment of the present invention, the medicament of the present invention can be used in preventing or treating A, B, C or D-stage heart failure according to the AHA/ACC stage classification Compound A, B and C and salts thereof may be a solvate or not. The solvate may be a solvent such as ethanol and water. If the solvent to be comprised is water, the solvate is a hydrate. The hydrate includes not only a stoichiometric hydrate but also hydrates different in water content.

Compound A, B and C and salts thereof may be labeled with an isotope (e.g., 3H, 13C, 14C, 18F, 35S, 125I).

Deuterides of compound A, B and C and salts thereof obtained by converting 1H with 2H (D) are also included.

Compound A, B and C and salts thereof may be in the form of a pharmaceutically acceptable co-crystal or co-crystalline salt. The co-crystal or co-crystal salt herein refers to a crystalline substance constituted of two types or more solids distinctive at room temperature and having mutually different physical properties (for example, structure, melting point, heat of fusion, hygroscopicity, solubility and stability). The co-crystal or co-crystalline salt can be produced by a co-crystallization method known per se.

Examples of the salts of compound A, B and C include a salt with an inorganic base, an ammonium salt, a salt with an organic base, a salt with an inorganic acid, a salt with an organic acid and a salt with a basic or acidic amino acid.

Preferable examples of the salt with an inorganic base include an alkali metal salt such as a sodium salt and a potassium salt; an alkaline earth metal salt such as a calcium salt, a magnesium salt, a barium salt; and an aluminum salt.

Preferable examples of the salt with an organic base include salts with trimethylamine, triethylamine, pyridine, picoline, ethanolamine, diethanolamine, triethanolamine, dicyclohexylamine and N, N'-dibenzylethylenediamine.

Preferable examples of the salt with an inorganic acid include salts with hydrochloric acid, hydrobromic acid, nitric acid, sulfuric acid and phosphoric acid.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid.

Preferable examples of the salt with a basic amino acid include salts with arginine, lysine and ornithine.

Preferable examples of the salt with an acidic amino acid include salts with aspartic acid and glutamic acid.

Of these salts, a pharmaceutically acceptable salt is preferable.

In a specific embodiment of the present invention, a salt of compound A can be a p-toluenesulfonate (tosylate) (hereinafter referred to also as "compound A'"). In a specific embodiment of the present invention, a salt of compound B can be a hydrochloride (hereinafter referred to also as "compound B'"). In a specific embodiment of the present invention, a salt of compound C can be a p-toluenesulfonate (tosylate) (hereinafter referred to also as "compound C'").

In a specific embodiment of the present invention, a compound selected from compound A, compound A', compound B, compound B', compound C and compound C' can be used for preventing or treating heart failure. In a specific embodiment of the present invention, compound A or compound A' can be used for preventing or treating heart failure. In a specific embodiment of the present invention, compound A' can be used for preventing or treating heart failure.

Compound A, B and C and salts thereof can be prepared by a method known per se (for example, method described in WO2004/017908 and Yoshida M. et al., Bioorg. Med. Chem., 19: 1881-1894, 2011, the contents of which are incorporated in the specification in their entirety by reference).

The dosage varies depending on e.g., the subject to be administered, administration route, disease and symptoms. For example, in the case of oral administration to a human (body weight about 50 kg), the dosage falls within the range of about 0.1 mg to about 500 mg in terms of compound A, B or C and preferably about 1 mg to about 100 mg. In the case of parenteral administration, the dosage can be selected from the range of about 0.01 mg to about 100 mg and preferably about 0.1 mg to about 10 mg. The dosage is administered in a single dose or several doses (for example, one to three per day).

The medicament of the present invention may comprise one compound selected from compound A, B and C and salts thereof, and a pharmaceutically acceptable carrier.

As the pharmaceutically acceptable carrier, various organic or inorganic carrier substances routinely used as a drug substance are used and blended as an excipient, a lubricant, a binder or a disintegrator in a solid preparation; a solvent, a solubilizer, a suspending agent, a tonicity agent, a buffer or a soothing agent in a liquid preparation. If necessary, a formulation additive such as a preservative, an antioxidant, a stabilizer, colorants or a sweetener can be used.

In an embodiment, the medicament of the present invention can be a medicament for parenteral administration or oral administration. The medicament of the present invention can be a medicament for oral administration.

The medicament of the present invention can be used in combination with another drug such as a drug for heart failure, for example, at least one of the following drugs:

(1) Therapeutic agent for heart failure
(i) β receptor antagonist (β blocker)
Carvedilol, metoprolol, atenolol, etc.
(ii) Diuretic agent
Hydrochlorothiazide, spironolactone, furosemide, indapamide, bendrofluazide, cyclopenthiazide, bumetanide, ethacrynic acid, etc.
(iii) Cardiotonic drug
Digitalis, digoxin, dobutamine, etc.
(iv) Anti-aldosterone drug
Spironolactone, eplerenone
(v) Heart rate lowering drug
Ivabradine, etc.
(vi) Intravenous cardiotonic drug
h-ANP, etc.
(vii) Angiotensin-converting enzyme inhibitor
Captopril, enalapril, delapril, etc.
(viii) Angiotensin II antagonist
Candesartan cilexetil, candesartan, losartan, eprosartan, valsartan, telmisartan, irbesartan, tasosartan, olmesartan, olmesartan medoxomil, azilsartan, azilsartan medoxomil, etc.
(ix) Others
Relaxin, etc.
(2) Others
(x) Ca-sensitivity enhancing agent
MCC-135, etc.
(xi) Ca channel antagonist
Nifedipine, diltiazem, verapamil, lomerizine hydrochloride, amlodipine besylate, etc.
(xii) Antiplatelet drug, anticoagulant
Heparin, aspirin, warfarin, dabigatran, rivaroxaban, pixaban, edoxaban, etc.
(xiii) HMG-CoA reductase inhibitor
Atorvastatin, simvastatin, etc.
(xiv) Uric acid lowering drug
Probenecid, allopurinol, febuxostat, etc.
(xv) Alpha blocking agent
Doxazosin, etc.
(xvi) Oral adsorbent
Kremezin, etc.
(xvii) Hyperkalemia therapeutic agent
Calcicol, etc.
(xviii) Hyperphosphatemia therapeutic agent
Sevelamer, lanthanum carbonate, etc.
(xix) Metabolic acidosis ameliorating drug
Sodium bicarbonate, etc.
(xx) Activated vitamin The medicament (drug) to be blended or used in combination with the medicament of the present invention includes both a medicament which is formulated as a single preparation comprising a compound selected from compound A, B and C and salts thereof and a drug used in combination (combination drug), and a medicament which is formulated as separate preparations: a preparation comprising a compound selected from compound A, B and C and salts thereof and a preparation comprising a combination drug (for example, combined medicament). Hereinafter, these will be collectively referred to simply as a combined medicament of the present invention.

The combined medicament of the present invention can be formulated by a method similar to that in the above-mentioned medicament comprising a compound selected from compound A, B and C and salts thereof by separately or simultaneously mixing a compound selected from compound A, B and C and salts thereof and a combination drug with or without a pharmaceutically acceptable carrier. The dosage of the combined medicament of the present invention per day varies depending on, e.g., the symptom; the age, sex, body weight and difference in sensitivity of the subject to be administered; timing and interval of administration, the feature, prescription and type of the medicament; and type of active ingredient and is not particularly limited.

In administering a combined medicament of the present invention, a compound selected from compound A, B and C and salts thereof and a combination drug may be administering at the same timing. Further, a combination drug is first administered, and then, a compound selected from compound A, B and C and salts thereof may be administered. Alternatively, a compound selected from compound A, B and C and salts thereof is first administered, and then, a combination drug may be administered. In the case of administering them at time intervals, the time interval varies depending on the active ingredient, dosage form and the administration method. For example, if a combination drug is first administered, a method of administering a compound selected from compound A, B and C and salts thereof within one minute to three days, preferably 10 minutes to one day, more preferably 15 minutes to 1 hour after a combination drug is administered, is mentioned as an approach. If a compound selected from compound A, B and C and salts thereof is first administered, a method of administering a combination drug within one minute to one day, preferably 10 minutes to 6 hours, more preferably 15 minutes to one hour after the compound is administered, is mentioned as an approach.

In combined medicament of the present invention comprising a compound selected from compound A, B and C and salts thereof concomitantly with a combination drug, the individual contents of the compound selected from compound A, B and C and salts thereof and the combination drug vary depending on the dosage form of the preparation of the combined medicament; however, the contents usually fall in the range of about 0.01 to 90 wt % relative, preferably about 0.1 to 50 wt % and further preferably about 0.5 to 20 wt % to the total amount of the preparation.

The content of the carrier in the combined medicament is usually about 0 to 99.8 wt %, preferably about 10 to 99.8 wt % and further preferably about 10 to 90 wt % relative to the total amount of the preparation.

In the case of a combined medicament, comprising a compound selected from compound A, B and C and salts thereof and a combination drug as separate preparations, the preparation comprising a combination drug can be produced in the same manner as in the compound selected from compound A, B and C and salts thereof, and put in use.

The medicament of the present invention may be either a solid preparation such as a powder, a granule, a tablet or a capsule, or a liquid such as a syrup or an emulsion.

The medicament of the present invention can be produced in accordance with a routine method including mixing, kneading, granulating, tableting, coating, sterilizing and emulsifying, depending on the dosage form of the preparation. Here, as to the production of the preparation, each section of General Rules for Preparations of the Japanese Pharmacopoeia, for example, can be referred. The medicament of the present invention may be formed as a sustained release agent comprising an active ingredient and a biodegradable polymer compound.

In an embodiment of the present invention, there is provided a medicament for preventing or treating heart failure in the subject in need thereof, comprising a compound selected from compound A, B and C and salts thereof and to be used in combination with a combination drug.

In another aspect of the present invention, there is provided a method for preventing or treating heart failure in a subject in need thereof, including administering a compound selected from compound A, B and C and salts thereof to the subject. In the method of the present invention, a heart failure to be treated can be any one of the diseases or disease states already described as those to be treated by the medicament of the present invention. In the method of the present invention, in the case where a compound selected from compound A, B and C and salts thereof is administered, a medicament comprising a compound selected from compound A, B and C and salts thereof may be administered.

In another aspect of the present invention, there is provided use of a compound selected from compound A, B and C and salts thereof for producing a medicament for preventing or treating heart failure in a subject in need thereof. Heart failure to be treated by the medicament can be any one of the diseases or conditions already described as those to be treated by the medicament of the present invention.

According to a specific embodiment of the present invention, the compound to be administered or the compound to be comprised in the medicament is a tosylate of compound A.

EXAMPLES

Compound A' was prepared in accordance with the method known in the art and described in WO2004/017908 and Yoshida M. et al., Bioorg. Med. Chem., 19: 1881-1894, 2011.

Calsequestrin (CSQ) cardiac specific transgenic mice (CSQ-Tg mice), which were reported in Larry R. Jones et al., J. Clin. Invest. 101: 1385-1393, 1998, were obtained from University of Pennsylvania, breeded in our company and put in use. In tests, using male and female mice, administration of a medicament was started on and after the mice reached 5 weeks old. The animals were raised in the conditions: room temperature: 20 to 26° c., humidity: 40 to 70%, illumination time: 12 hours/day (7:00-19:00) by giving a solid feed (CE-2, manufactured by CLEA Japan, Inc.) and tap water. In the CSQ-Tg mice, as already reported, $Ca^{2+}$ intracellular release was suppressed; myocardial contraction declined and cardiac output decreased. Cardiac hypertrophy and heart failure developed.

Example 1: Atrial Weight Reduction Effect of Compound A' in Heart Failure Model Animal In this example, using CSQ-Tg mice as a heart failure model animal, the atrial weight reduction effect of compound A' was evaluated.

Compound A' was suspended (10 mL/kg) in a 0.5% aqueous methylcellulose solution (hereinafter in Examples, sometimes referred to as a "vehicle") and orally administered to CSQ-Tg male mice of 5 weeks old with heart failure in a dosage of 30 mg/kg body weight/day once per day (QD) for 14 days (n=7). To negative control (vehicle administration group) mice, a 0.5% aqueous methylcellulose solution was administered (n=9). Thereafter, the atrial weight of the mice was measured. The results were as shown in Table 4.

TABLE 4

| Left atrial weight | Average value (mg) | Standard deviation (mg) |
| --- | --- | --- |
| Vehicle administration group | 12.6 | 4.4 |
| Compound A' administration group | 8.4 | 1.0 |

As shown from Table 4, it was found that, in the Compound A' administration group, the left atrial weight (mg) decreases, and significant difference was confirmed by the t-test (p<0.05). From the results, it was demonstrated that compound A' has an improvement effect (atrial weight reduction effect) on heart remodeling in heart failure.

Example 2: Improvement Effect of Compound A' on Left Ventricular Hypertrophy and Lung Weight Increase In this example, the effect of compound A' in improving left ventricular hypertrophy and lung weight increase caused by heart failure was examined.

Compound A' was suspended in a 0.5% aqueous methylcellulose solution (10 mL/kg) and orally administered to CSQ-Tg female mice of 5 weeks old with heart failure in a dosage of 30 mg/kg body weight/day once per day (QD) for 14 days (n=10). To negative control (vehicle administration group) mice, a 0.5% aqueous methylcellulose solution was administered (n=10). Thereafter, lung weight (Lung), left-ventricle weight (LV) and body weight (BW) were individually measured and were standardized with the BW. The results were as shown in Table 5.

TABLE 5

| Average value ± standard deviation | LV/BW | Lung/BW |
|---|---|---|
| Vehicle administration group | 9.3 ± 1.6 | 8.1 ± 1.3 |
| Compound A' administration group | 7.9 ± 1.0 | 6.8 ± 1.3 |

As shown in Table 5, in the Compound A' administration group, the lung weight and left ventricular weight both statistically significantly decreased (t-test, both $p<0.05$). From the results, it was demonstrated that compound A' improves left ventricular hypertrophy and lung weight increase.

Example 3: Effect of Compound A' on Survival Rate of Heart Failure Model Animals In this example, effect of compound A' on survival rate of heart failure model animals was examined.

Compound A' was orally administered to CSQ-Tg female mice (n=30) of 5 weeks old in a dosage of 30 mg/kg body weight/day once per day (QD) for 30 days. To negative control (vehicle administration group) mice, a 0.5% aqueous methylcellulose solution was administered (n=30). The results were as shown in FIG. 1.

As shown in FIG. 1, the survival rate of the compound A' administration group was significantly improved compared to the vehicle group (log-rank test, $p<0.001$). From this, it was demonstrated that compound A' improves the condition of heart failure. This is the effect of compound A' in improving death of decreased cardiac function by overexpression of Calsequestrin.

From the above results of Examples, it is understood that compound A' improves ejection fraction in a subject with heart failure and can treat heart failure in this mechanism. It was found that compound A' at least has an effect of reducing cardiac load of the heart in failure and an effect of improving cardiac function or inhibiting exacerbation of cardiac function by suppressing myocardial hypertrophy, interstitial fibrosis, apoptosis and the like. Based on this, it is interpreted that compound A' has not only a therapeutic effect but also a preventive effect on heart failure.

INDUSTRIAL APPLICABILITY

According to the present invention, there is provided a medicament for preventing or treating heart failure. Thus, the invention is useful.

The contents of cited literatures such as scientific literatures, Japanese Patents and Japanese Patent Applications are incorporated herein in their entirety by reference to the same extents that they are specifically described.

This application claims for the priority based on Japan Japanese Patent Application No. 2015-253809 (filed on Dec. 25, 2015), the contents of which are incorporated herein by reference.

The invention claimed is:

1. A method for treating heart failure in a subject having heart failure, comprising administering to the subject a compound selected from the group consisting of
   (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide,
   (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, and
   (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide or a salt thereof.

2. The method of claim 1, wherein the heart failure is acute decompensated heart failure.

3. The method of claim 1, wherein the compound is (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, or a p-toluenesulfonate salt thereof.

4. The method of claim 1, wherein the compound is (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, or a hydrochloride salt thereof.

5. The method of claim 1, wherein the compound is (5R)-N-[1-ethyl-1-(4-ethylphenyl)propyl]-5-(2-fluorophenyl)-2,7,7-tri methyl-4,5,6,7-tetrahydropyrazolo[1,5-a]pyrimidine-3-carboxamide, or a p-toluenesulfonate salt thereof.

6. The method of claim 1, further comprising administering to the subject an additional drug for treating heart failure.

* * * * *